(12) United States Patent
Danhamer et al.

(10) Patent No.: US 9,025,155 B2
(45) Date of Patent: May 5, 2015

(54) HAND-HELD COLOR MEASUREMENT DEVICE

(71) Applicants: Bernd Danhamer, Niederweningen (DE); Lido Feri, Baden (CH); Marco Kessler, Hägglingen (CH)

(72) Inventors: Bernd Danhamer, Niederweningen (DE); Lido Feri, Baden (CH); Marco Kessler, Hägglingen (CH)

(73) Assignee: X-Rite Europe GmbH, Regensdorf (CH)

( * ) Notice: Subject to any disclaimer, the term of this patent is extended or adjusted under 35 U.S.C. 154(b) by 0 days.

(21) Appl. No.: 14/013,170

(22) Filed: Aug. 29, 2013

(65) Prior Publication Data

US 2014/0063500 A1  Mar. 6, 2014

(30) Foreign Application Priority Data

Sep. 4, 2012 (EP) .................................. 12182902

(51) Int. Cl.
*G01N 21/55* (2014.01)
*G01N 21/25* (2006.01)
*G01J 3/50* (2006.01)
*G01J 3/02* (2006.01)

(52) U.S. Cl.
CPC .............. *G01N 21/255* (2013.01); *G01J 3/504* (2013.01); *G01J 3/0289* (2013.01); *G01J 3/0272* (2013.01); *G01N 21/251* (2013.01); *G01N 2201/0221* (2013.01)

(58) Field of Classification Search
CPC .... G01N 21/553; G01N 21/554; G01N 21/55
See application file for complete search history.

(56) References Cited

U.S. PATENT DOCUMENTS 7,027,160 B2 * 4/2006 Sperling ....................... 356/446
2006/0114465 A1 * 6/2006 Hart et al. ..................... 356/445

FOREIGN PATENT DOCUMENTS

| DE | 19633557 A1 | 3/1998 |
| DE | 10018982 A1 | 10/2001 |
| DE | 102004034167 A1 | 2/2006 |
| EP | 1655589 A2 | 5/2006 |
| JP | 5256772 | 5/1993 |

OTHER PUBLICATIONS

European Search Report, dated Apr. 2, 2013.

* cited by examiner

*Primary Examiner* — Michael P Stafira
(74) *Attorney, Agent, or Firm* — McCarter & English, LLP

(57) ABSTRACT

A hand-held color measurement device is provided that is designed especially for measurements on curved surfaces includes a housing that accommodates a measurement array and further includes a housing base and a measurement opening arranged in the housing base, through which measurement opening a measurement spot on the surface of a measurement object is illuminated and the measurement light reflected by the measurement spot is picked up. The measurement array includes an illumination array for applying illumination light to the measurement spot in at least one illumination direction, and a pick-up array for detecting the measurement light in at least one observation direction. A multi-point bearing includes at least three pin-shaped support members and is arranged on the housing base. Two support members lie symmetrically on both sides of the measurement opening, wherein their connecting line extends parallel to and in the immediate vicinity of an illumination-observation plane which is defined by the illumination and observation directions. The third support member lies transversely at a distance from the other two support members.

7 Claims, 9 Drawing Sheets

HAND-HELD COLOR MEASUREMENT DEVICE

BACKGROUND

1. Technical Field

The invention relates to a hand-held color measurement device with particular applicability in making measurements on curved surfaces.

2. Background Art

Hand-held color measurement devices of the type under discussion can be embodied, irrespective of the underlying measurement technology, as autonomous devices or as peripheral measurement devices for use in connection with a controlling computer which evaluates measurement data. Autonomous color measurement devices contain all the operating and display members necessary for measurement operations and also their own power supply and are in many cases also equipped with an interface for communicating with a computer, wherein both measurement data and control data can be exchanged with the computer. Color measurement devices which are configured as peripheral measurement devices do not generally have their own operating and display members and are controlled by the superordinate computer like any other peripheral computer device. For communicating with a computer, more modern color measurement devices are often for example fitted with a so-called USB (universal serial bus) interface, via which in many cases it is simultaneously also possible to supply power (from the attached computer).

Metallic paints and paints containing effect pigments are being used more and more nowadays, not only in the automobile industry. Such paints show a significant angular dependence. Paints containing aluminum flakes, for example, show a significant brightness flop. Paints containing interference effect pigments also show differences in color when the observation or illumination direction is changed. Multi-angle measurement devices have become established for measuring such paints. Measuring brilliance is a related topic, in which the measurement result is likewise angle-sensitive.

Measurement devices which can detect such properties have to be embodied to illuminate the measurement object at one or more different, exactly defined illumination directions (in relation to the normal onto the measurement object in the measurement spot) and to pick up the light reflected by the measurement object from at least one exactly defined observation direction (likewise in relation to the normal onto the measurement object in the measurement spot). The observation direction and the illumination direction can be exchanged. A measurement array comprising at least one illumination direction and a number of observation directions is common in practice.

One typical area of application for such color measurement devices is in the automobile industry and concerns gauging paints on vehicle body parts at a number of angles, in terms of their color and possibly additional aspects of their appearance.

One great difficulty within this application is that it is often necessary to measure on curved surfaces. If the measurement device is not placed exactly and reproducibly on the curved measurement surface, this results in deviations in the usually very narrow-tolerance illumination and observation directions, which in turn leads to distortions in the measurement values.

Hand-held color measurement devices are already known which are equipped with special bearing means for placing the devices on curved measurement objects. One known hand-held color measurement device has a bearing means in the form of an annular collar which surrounds the measurement opening. This bearing means, however, is only suitable for regular curved surfaces. Other hand-held color measurement devices are equipped with sensors which indicate to the user how he or she has to position the hand-held color measurement device. This bearing means is on the one hand relatively complicated and on the other hand requires the active involvement of the user.

It is then the intention of the present invention to improve a hand-held color measurement device of the generic type to the effect that it can be securely and reproducibly placed even onto curved measurement objects using very simple means, such that the predefined illumination and observation directions are exactly maintained and distortions in the measurement values thus avoided.

This object on which the invention is based is solved by the hand-held color measurement device in accordance with the invention, as characterized by the features of independent claim 1. Advantageous embodiments and developments of the hand-held color measurement device in accordance with the invention are the subject-matter of the dependent claims.

SUMMARY

The essence of the invention is as follows: a hand-held color measurement device comprises a housing, wherein said housing accommodates a measurement array and an electronic controller and comprises a housing base and a measurement opening through which a measurement spot on a surface of a measurement object is illuminated and the measurement light reflected by the measurement spot is picked up. The measurement array comprises an illumination array for applying illumination light to the measurement spot in at least one illumination direction, and a pick-up array for detecting the measurement light in at least one observation direction. The at least one illumination direction and the at least one observation direction lie in a common illumination-observation plane. The housing base of the housing comprises a bearing means for positioning the device on the surface to be gauged. The bearing means is embodied as a multi-point bearing comprising at least three substantially pin-shaped support members, each comprising a bearing area, wherein the bearing areas of a first and a second support member lie in a base line which extends parallel to the illumination-observation plane at a distance of at most 2 mm from it, wherein the bearing areas of all the other support members are arranged at a distance from the illumination-observation plane which is greater than the distance of the first and/or second support member, and wherein the bearing areas of the support members lie substantially in a base plane which is perpendicular to the illumination-observation plane.

Embodying the bearing means as a multi-point bearing allows the measurement device to be positioned securely on both level and curved surfaces of measurement objects.

The hand-held color measurement device reacts very sensitively in the illumination-observation plane to incorrect positioning which exhibits angular errors, but significantly less so transverse to the illumination-observation plane. Arranging, in accordance with the invention, two pin-shaped support members in said base line in the immediate vicinity of the illumination-observation plane ensures that the illumination and observation directions relative to the measurement spot and/or the normal onto the measurement spot remain largely independent of the surface curvature of the measurement object, at least in the illumination-observation plane. In this way, distortions in the measurement values caused by the surface curvature of the measurement object are largely avoided. Due to the specific arrangement of the support members in accordance with the invention, any angular errors all come to rest in the non-sensitive direction transverse to the illumination-observation plane, and practically no angular errors arise in the crucial illumination-observation plane.

In accordance with a particularly advantageous embodiment, the first and the second support member are arranged on both sides of the measurement opening and substantially symmetrically with respect to it. This additionally helps to avoid distortions in the measurement values.

Preferably, the bearing areas of the support members are each smaller than 20 mm$^2$, preferably smaller than 10 mm$^2$ and in particular smaller than 5 mm$^2$.

In accordance with an advantageous embodiment, the bearing means is embodied as a three-point bearing comprising three substantially pin-shaped support members. This provides optimum stability for the hand-held color measurement device.

The distance between the base line and the illumination-observation plane advantageously measures at most 1 mm, preferably at most 0.5 mm and in particular 0 mm. The small to infinitesimal distance from the illumination-observation plane crucially helps to avoid distortions in the measurement values due to surface curvatures of the measurement object.

In accordance with another advantageous embodiment, a projection of the center of gravity of the device in relation to the base plane lies in a direction perpendicular to the base plane between the bearing areas of the support members. This arrangement of the center of gravity of the device allows the measurement device to stand stably and reduces the danger of the device tilting.

The pin-shaped support members are advantageously equipped with sensors, in particular pressure sensors and/or force sensors, which cooperate with the controller in such a way as to monitor and signal whether all the support members are correctly placed on the surface of the measurement object. This prevents measurement errors from being able to arise if the measurement device is unintentionally tilted.

BRIEF DESCRIPTION OF FIGURES

In the following, the invention is explained in more detail on the basis of the drawings, which show.

DESCRIPTION OF EXEMPLARY EMBODIMENT(S)

The following provision applies to the following description of the figures: where individual reference signs are not indicated in a figure, reference is then made in this respect to the other figures and to the corresponding parts of the description. The abbreviated terms "color measurement device" and "measurement device" are always understood to mean a hand-held color measurement device. The term "measurement array" is understood to mean the sum of the components of the hand-held color measurement device which serve to illuminate a measurement spot on the surface of a measurement object and to detect the light reflected by this measurement spot and to convert it into corresponding electrical signals.

Figure 1:
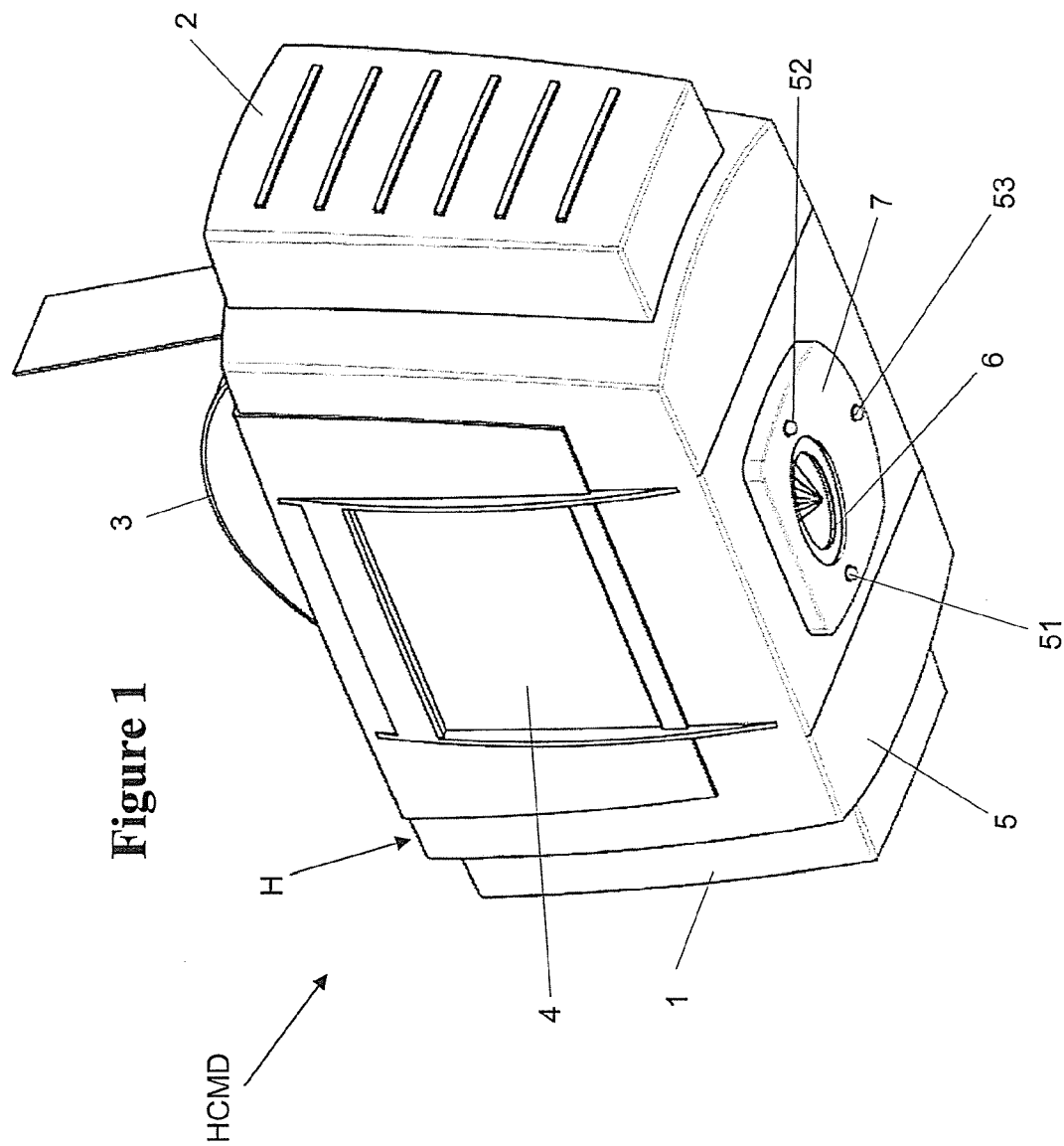
FIG. 1 an oblique view of an example embodiment of the hand-held color measurement device in accordance with the invention.
Figure 6:
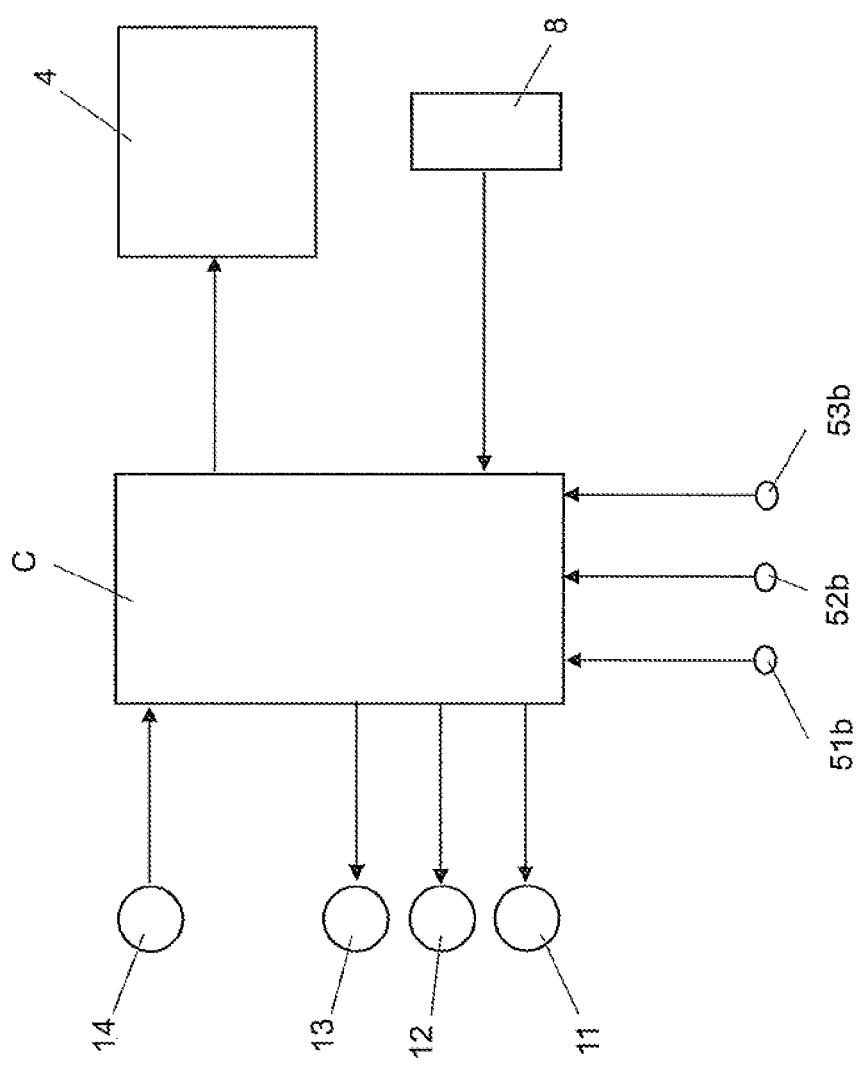
FIG. 6 a block diagram of the optical and electronic components of the hand-held color measurement device.

The hand-held color measurement device shown in FIG. 1 is indicated as a whole by the reference sign HCMD. It comprises a housing H which accommodates a measurement array MA and an electronic control array C (FIG. 6) which controls the measurement array MA. Two gripping parts 1 and 2 are embodied laterally on the housing H. A wrist strap 3 is arranged on the upper side of the housing H. A display array 4 is provided on the front side of the housing H. Operating members 8, shown schematically in FIG. 6, are also arranged on the upper side of the housing H.

The lower side of the housing H comprises a housing base 5 which is reinforced by a base plate 7 which is provided with a measurement opening 6. The housing base 5 comprises an aperture 7a (FIG. 2) in the region of the measurement opening 6, such that light can exit the interior of the housing through the aperture 7a and, conversely, light from outside can enter the interior of the housing through the measurement opening 6 and the aperture 7a.

Figure 2:
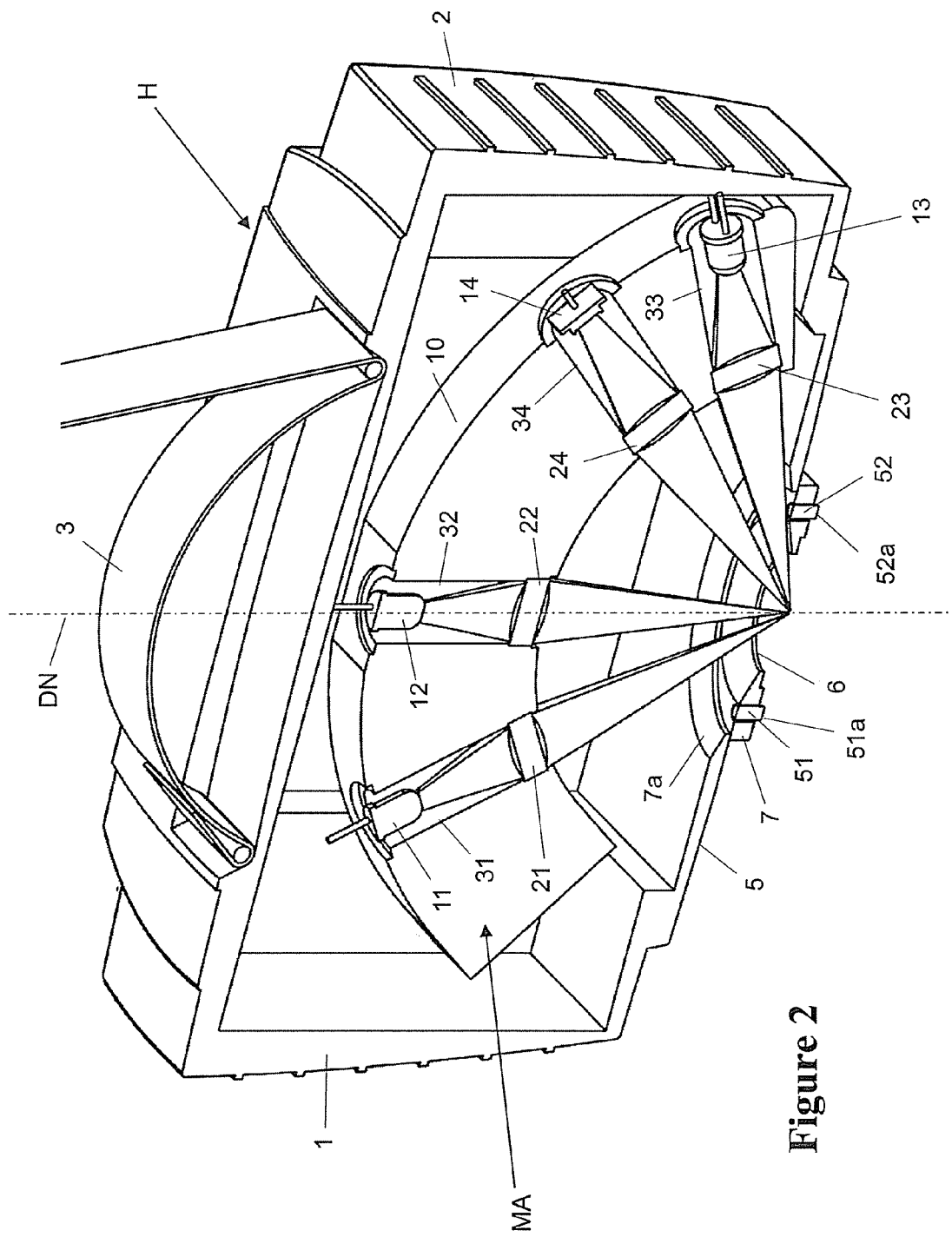
FIG. 2 a vertical section through the hand-held color measurement device of FIG. 1.
Figure 3:
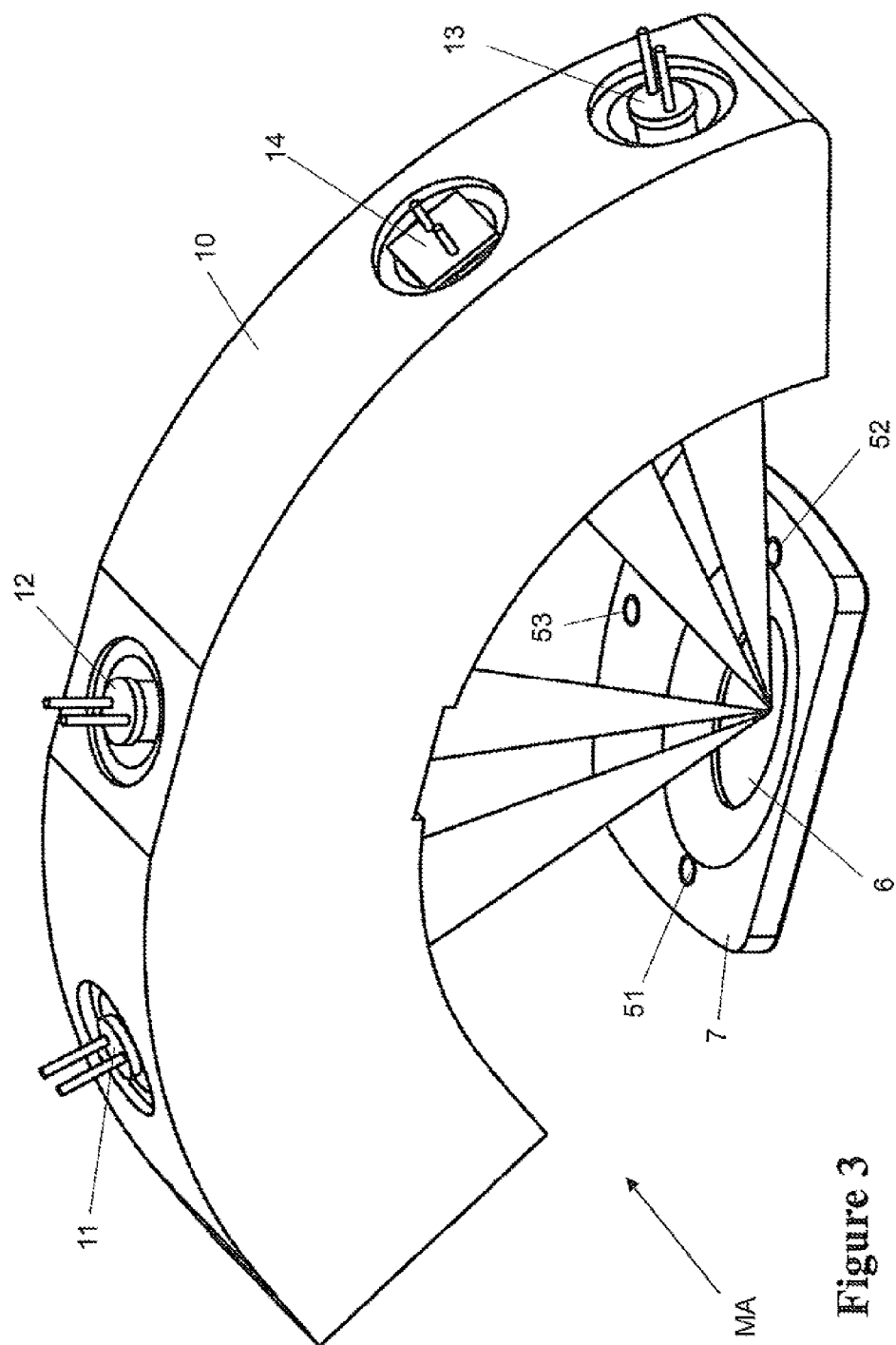
FIG. 3 an oblique view of the measurement array of the hand-held color measurement device.
Figure 4:
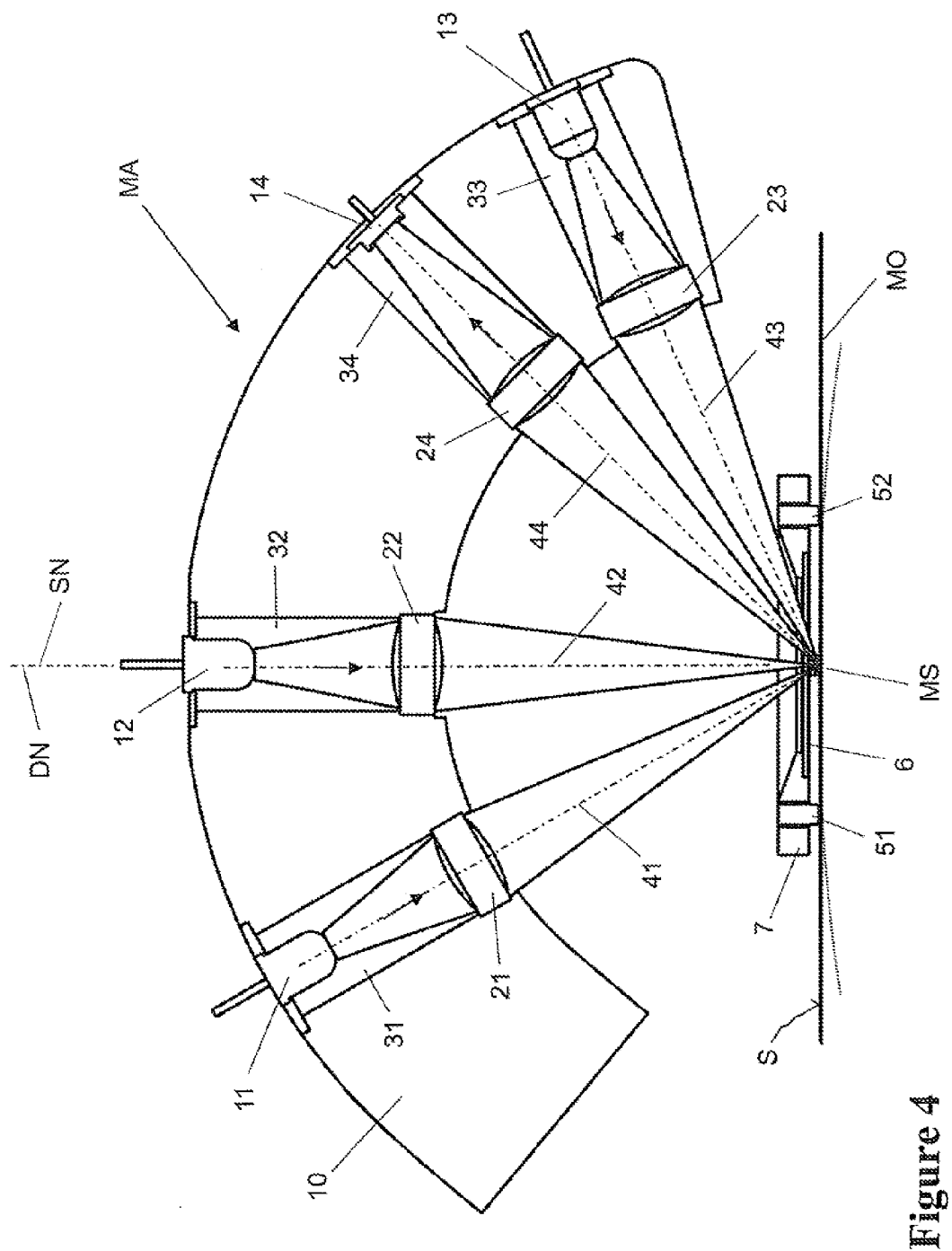
FIG. 4 a vertical section through the measurement array of FIG. 3.

The embodiment of the measurement array MA can be seen from FIGS. 2 to 4. It comprises an arc body 10 which is attached, spatially fixed, in the housing H and in which all the optical and/or photoelectric components of the measurement array MA are arranged in continuous chambers. In the example embodiment shown, these components consist of three light sources 11, 12 and 13, for example in the form of LEDs, and a light converter in the form of a color-enabled camera 14 comprising respectively assigned lens systems 21, 22, 23 and 24. Correspondingly, the arc body 10 comprises four chambers 31 to 34. The light sources 11, 12 and 13 together with the lens systems 21, 22 and 23 assigned to them form an illumination array for illuminating a measurement spot MS in three illumination directions. Correspondingly, the light converter 14 together with the lens system 24 assigned to it forms a pick-up array for light reflected by the measurement spot MS in an observation direction.

The optical axes of the beam paths emitted by the light sources 11, 12 and 13 and leading to the light converter 14 are indicated by 41, 42 43 and 44. The optical axes 41, 42 and 43 each define a nominal illumination direction; the optical axis 44 defines a nominal observation direction. The measurement array MA as a whole is arranged such that the optical axes 41, 42 43 and 44 and/or the illumination directions and the observation direction are situated in a common plane which is referred to in the following as the illumination-observation plane 40 (FIG. 5) and is perpendicular to the base plate 7 and/or the measurement opening 6 situated therein. In the example embodiment shown, the illumination and pick-up beam paths are embodied linearly. It is however also possible, for example for reasons of space, to deviate one or more of the beam paths, i.e. for example to deflect one or more of the beam paths by means of mirrors. It is essential only that the optical axes of the beam path portions which lead directly towards and/or away from the measurement spot lie in a common illumination-observation plane.

The light sources 11, 12 and 13 are controlled by the computer-based control array C. The latter also controls the light converter and/or camera 14 and processes its measurement signals. The control array C displays measurement results on the display array 4 and receives operating commands from the operating members 8.

The measurement array MA can also be conversely embodied with respect to the illumination and observation directions. Specifically, this means that the measurement object would be illuminated at one defined illumination direction only, and the reflected measurement light would instead be picked up at three different observation directions. Any combinations of one or more illumination directions and one or more observation directions are of course also possible.

In FIG. 2, a device normal DN is also indicated. This is an (imaginary) straight line which extends through the center point of the measurement opening 6 and/or the intersection point of the optical axes 41, 42 43 and 44 and is perpendicular to the plane of the measurement opening 6 and/or the base plate 7 which contains it. If a measurement object MO has a level surface S, the device normal DN coincides with an (imaginary) surface normal SN (FIG. 4) which extends through the center point of the measurement spot MS and is perpendicular to the surface S.

To this extent, the color measurement device described corresponds in principle to conventional color measurement devices of this type, such that the person skilled in the art does not require any further explanation in this respect.

The present invention is not concerned with the actual measurement technology and evaluating the measurement results but rather with the problems of positioning the measurement device on curved surfaces. This is discussed in more detail in the following.

Figure 5:
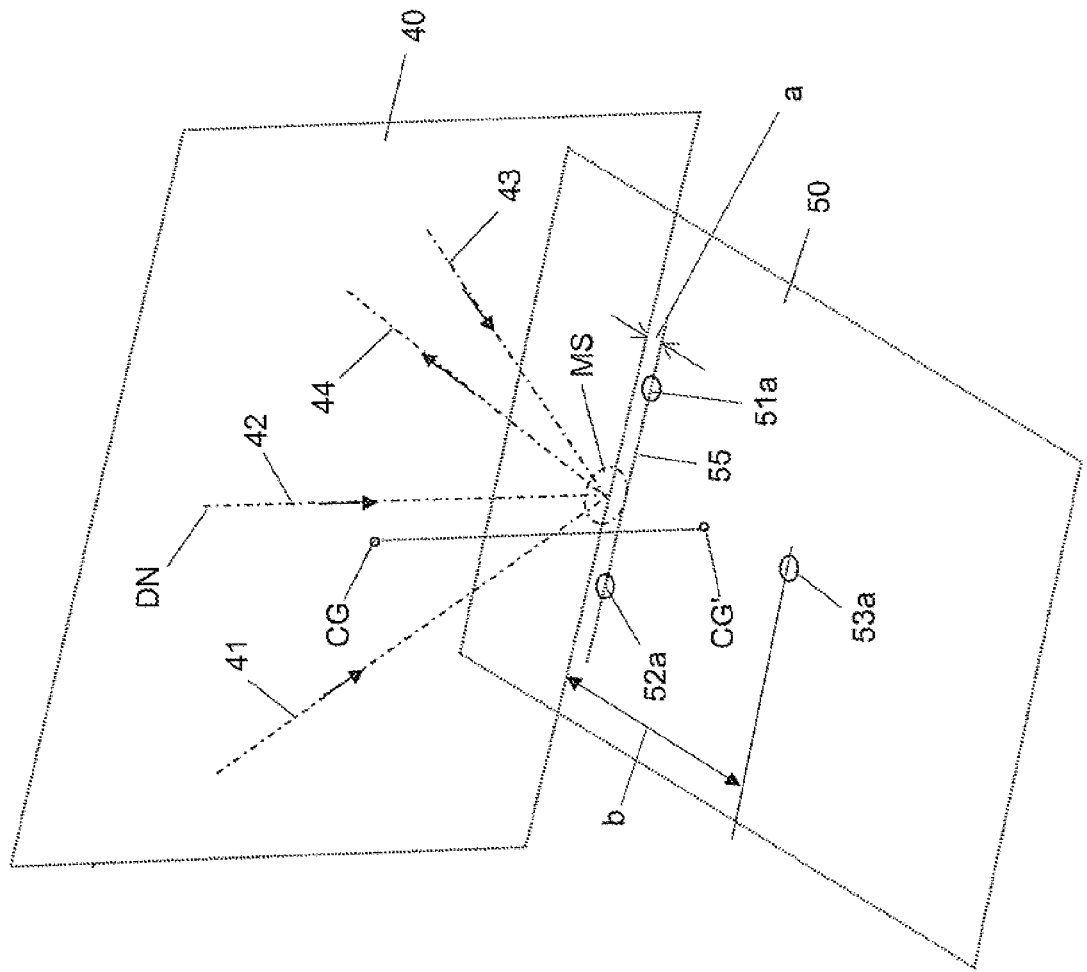
FIG. 5 a sketch to illustrate the reciprocal locations of the measurement array and the support members of the hand-held color measurement device.
Figure 8:
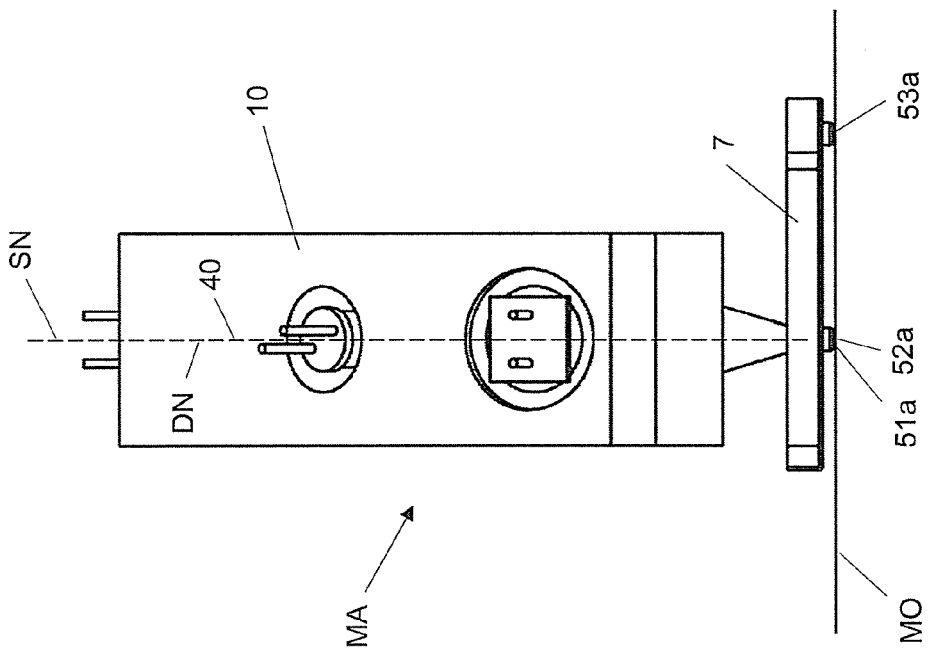

In accordance with a first important aspect of the invention, the housing base 5 of the measurement device is equipped with a bearing means which is embodied as a multi-point bearing. In the example embodiment shown, the bearing means specifically consists of three pin-shaped support members 51, 52 and 53 which are attached in the base plate 7 and protrude out of and perpendicular to it. The three pin-shaped support members 51, 52 and 53 each comprise a bearing area 51a, 52a and 53a (FIGS. 2, 5 and 8). The lengths of the portions of the three support members 51, 52 and 53 which protrude out of the base plate 7 are all identical and measure a few millimeters. The bearing areas 51a, 52a and 53a of the three support members 51, 52 and 53 lie in a common plane which extends parallel to the base plate 7 and/or the measurement opening 6 situated therein and perpendicular to the illumination-observation plane 40 and which is referred to in the following as the base plane 50 (FIG. 5). The sizes and/or areas of the bearing areas 51a, 52a and 53a of the three support members 51, 52 and 53 are smaller than 20 mm$^2$, preferably smaller than 10 mm$^2$ and in particular smaller than 5 mm$^2$.

In accordance with another important concept of the invention, two pin-shaped support members 51 and 52 are arranged such that the center points of their bearing areas 51a and 52a lie on a base line 55 which lies in the base plane 50 and extends in parallel at a small distance a from the illumination-observation plane 40 (FIG. 5). The third support member 53 and/or its bearing area 53a is situated at a distance b from the illumination-observation plane 40 which is greater than the distance a of the first and/or second support member. The distance a between the base line 55 and the illumination-observation plane measures at most 2 mm, preferably at most 1 mm and especially at most 0.5 mm and is ideally equal to 0, i.e. the base line 55 coincides with the illumination-observation plane 40. The two support members 51 and 52 situated on the base line 55 are preferably arranged symmetrically on both sides of the measurement opening 6 and/or the measurement spot MS; their reciprocal distance measures for example about 10 to 40 mm. The distance b between the third support member 53 and the illumination-observation plane 40 measures for example about 15 to 40 mm.

In FIG. 5, the three support members 51, 52 and 53 are all situated on the same side of the illumination-observation plane 40. The first and second support members 51 and 52 on the one hand and the third support member 53 (and any other support members) on the other hand can of course also lie on different sides of the illumination-observation plane 40, as is shown in the example embodiments of FIGS. 10 and 11.

In accordance with another important concept of the invention, the measurement device is designed with respect to the arrangement and weight distribution of its components in such a way that its center of gravity CG in relation to the base plane 50 lies between the pin-shaped support members 51, 52 and 53. In other words, a projection CG' of the center of gravity CG of the device then lies in a direction perpendicular to the base plane 50 within a triangle defined by the three bearing areas 51a, 52a and 53a of the three support members 51, 52 and 53 (FIG. 5). If there are more than three support members, the same applies analogously. This arrangement of the center of gravity CG of the device allows the measurement device to stand stably and reduces the danger of the device tilting.

Figure 7:
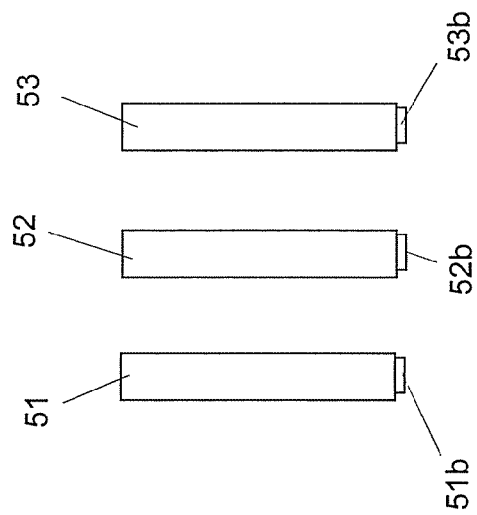
FIG. 7 an embodiment variant of the support members of the hand-held color measurement device in accordance with the invention.

In accordance with a particularly expedient embodiment of the measurement device in accordance with the invention, the pin-shaped support members 51, 52 and 53 are equipped with sensors 51b, 52b and 53b which cooperate with the controller C and enable the correct positioning of the measurement device on the surface S of the measurement object MO to be monitored (FIG. 6 and FIG. 7). Correct positioning is understood to mean that all the support members 51, 52 and 53 are positioned on the surface of the measurement object. The sensors 51b, 52b and 53b can for example be embodied as pressure sensors and/or force sensors and in particular as pressure switches. The controller C can be configured such that it indicates to the user, for example via the display array 4 or separate signal lamps, when the measurement device is and/or is not correctly positioned.

Embodying the bearing means as a multi-point bearing allows the measurement device to be positioned securely on both level and curved surfaces of measurement objects. Arranging, in accordance with the invention, two pin-shaped support members in said base line in the immediate vicinity of the illumination-observation plane ensures that the illumination and observation directions relative to the measurement spot MS and/or the surface normal SN onto the measurement spot MS remain largely independent of the surface curvature of the measurement object, at least in the angle-sensitive illumination-observation plane 40. In this way, distortions in the measurement values caused by the surface curvature of the measurement object are largely avoided.

FIG. 8 shows a measurement device which is placed onto a measurement object MO which is level and/or cylindrically curved about an axis which is perpendicular to the illumination-observation plane 40. For the sake of clarity, the only parts of the measurement device shown are the measurement array MA and the base plate 7. As can be seen, the surface normal SN onto the center of the measurement spot coincides with the illumination-observation plane 40.

Figure 9:
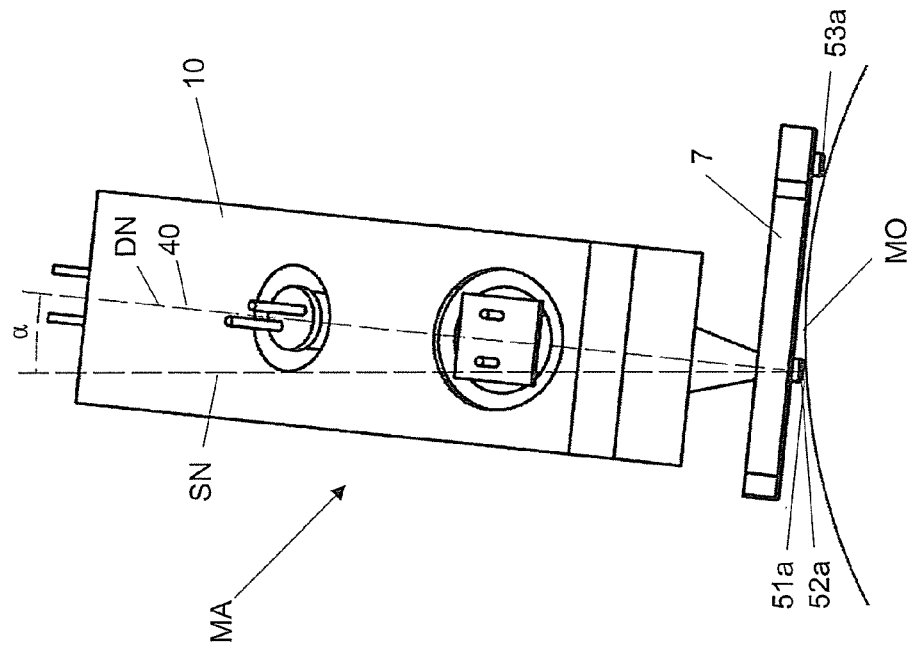
FIGS. 8-11 four sketches to illustrate how the hand-held color measurement device is used in practice.

FIG. 9 shows an analogous representation of the measurement device, in which however the measurement object MO is (additionally) curved transverse to the illumination-observation plane 40. In this case, the normal SN is tilted out of the illumination-observation plane 40 by a tilting angle α. This relatively small tilting angle does not however have any substantial influence on the measurement result and is in any case less crucial than a tilt within the illumination-observation plane 40.

The advantages of the multi-point bearing in accordance with the invention are particularly brought to bear in the case of asymmetrically or irregularly curved surfaces of the measurement object. Arranging, in accordance with the invention, two pin-shaped support members in said base line in the immediate vicinity of the illumination-observation plane ensures that the illumination and observation directions relative to the measurement spot and/or the normal onto the measurement spot remain largely independent of the surface curvature of the measurement object in the illumination-observation plane. Due to the specific arrangement of the support members in accordance with the invention, any angular errors all come to rest in the non-sensitive direction transverse to the illumination-observation plane, and practically no angular errors arise in the crucial illumination-observation plane.

Figure 10:
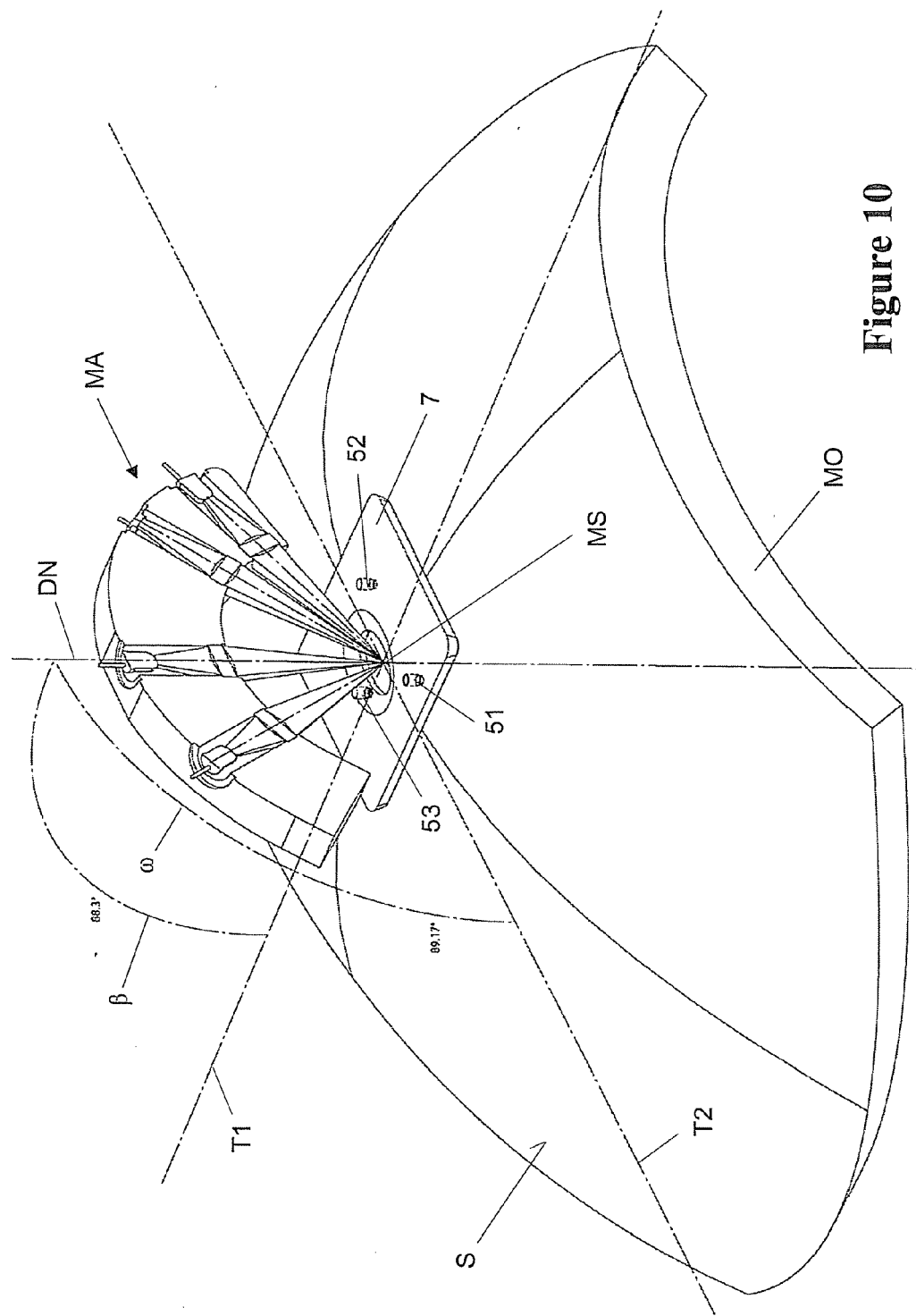
Figure 11:
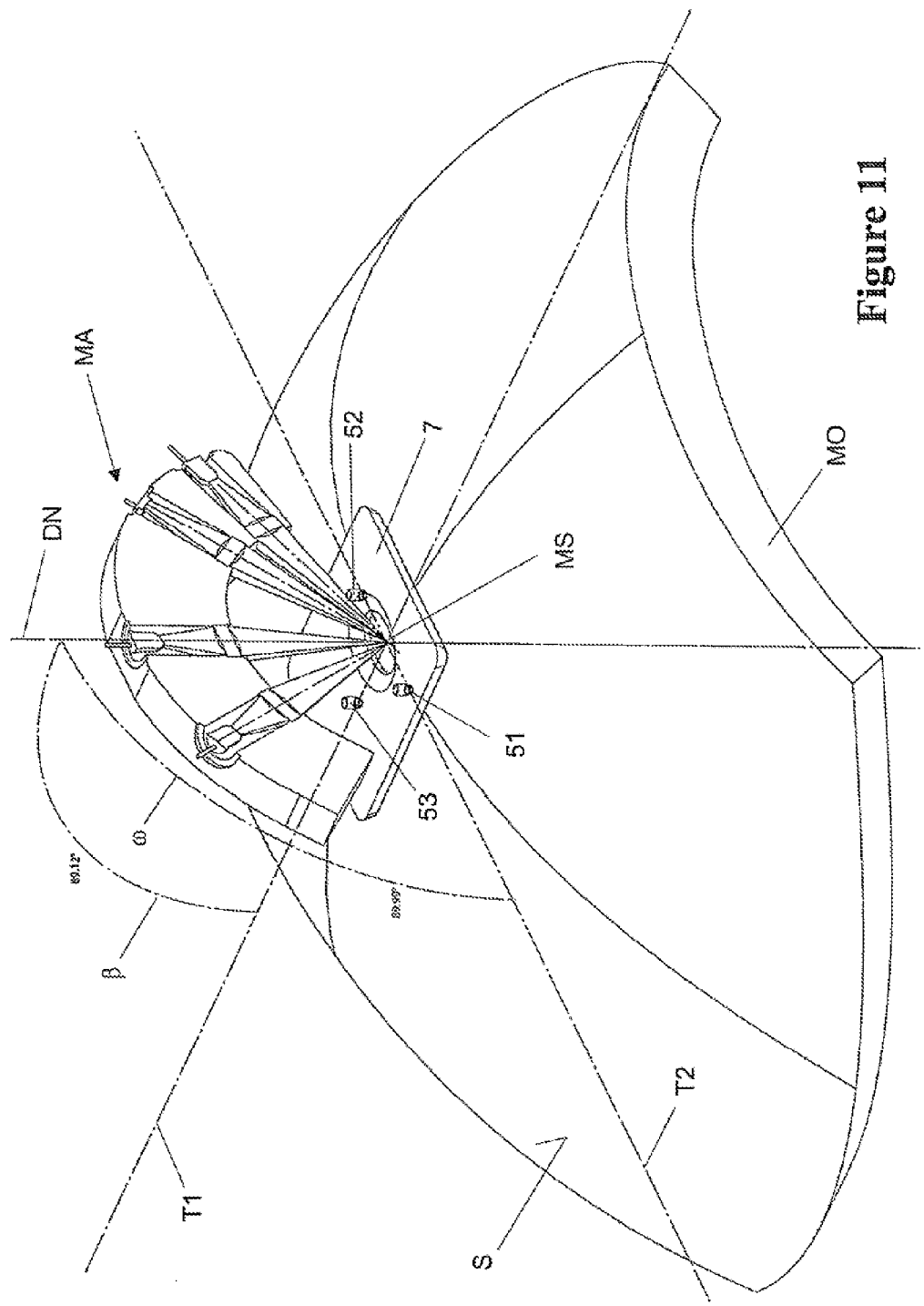

FIGS. 10 and 11 illustrate how the color measurement device in accordance with the invention is used in practice on a measurement object MO which comprises a two-dimensionally curved surface S. For the sake of clarity, the only parts of the measurement device shown are the measurement array MA together with the base plate 7 and the support members 51, 52 and 53 arranged in it. The two mutually orthogonal dot-dash lines T1 and T2 indicate a tangential plane onto the surface S in the center of the measurement spot MS; the dot-dash line DN is the device normal which has already been mentioned further above and which extends through the center of the measurement opening. The two angles $\beta$ and $\omega$ between the device normal DN and the line T1 on the one hand and the line T2 on the other hand illustrate the spatial location of the measurement array MA relative to the surface S of the measurement object MO. The angle $\omega$ is a measure of the tilt of the measurement array MA in the illumination-observation plane (not shown); the angle $\beta$ is a measure of the tilt of the measurement array MA out of the illumination-observation plane, wherein 90.0° respectively signifies the ideal state with no tilt.

In FIG. 10, the three-point bearing of the measurement device is embodied such that the two support members 51 and 52 are situated at a relatively large distance from the illumination-observation plane (not shown) of the measurement array MA. A significant tilt (deviation from the ideal state of 90.0°) can be seen here, wherein the tilt is however still significantly smaller in the illumination-observation plane (the angle $\omega=89.17°$) than in a direction transverse to the illumination-observation plane (the angle $\beta=88.3°$).

In the example embodiment of FIG. 11, the two support members 51 and 52 lie in and/or at a very small distance from the illumination-observation plane (not shown) of the measurement array MA. As can be seen here, the tilt of the measurement array in the illumination-observation plane (the angle $\omega=89.99°$) is practically infinitesimal, and the tilt in a direction transverse to the illumination-observation plane (the angle $\beta=89.12°$) is likewise relatively small.

Although a three-point bearing comprising three pin-shaped support members is optimum, it is of course also possible to provide more than three support members, as long as the configuration conditions described above are fulfilled. Specifically, this means that two support members lie on the base line in the immediate vicinity of the illumination-observation plane, and the other support members have to be situated transversely at a greater distance from the illumination-observation plane.

Although the present invention has been described with reference to exemplary implementations thereof, it is to be understood that the invention is not limited by or to these exemplary implementations. Rather, the present invention is susceptible to various implementations without departing from the spirit or scope of the present invention, as will be readily apparent to persons skilled in the art.

The invention claimed is:

1. A hand-held color measurement device comprising:
a housing, wherein said housing accommodates a measurement array and an electronic controller and comprises a housing base and a measurement opening through which a measurement spot on a surface of a measurement object is illuminated and the measurement light reflected by the measurement spot is picked up,
wherein the measurement array comprises an illumination array for applying illumination light to the measurement spot in at least one illumination direction, and a pick-up array for detecting the measurement light in at least one observation direction,
wherein the at least one illumination direction and the at least one observation direction lie in a common illumination-observation plane, and wherein the housing base of the housing comprises a bearing means for positioning the device on the surface to be gauged,
wherein the bearing means is embodied as a three-point bearing having three substantially pin-shaped support members, each comprising a bearing area, wherein the bearing areas of a first and a second one of the support members lie in a base line which is in the illumination-observation plane at a distance of at most 2 mm from it, wherein the bearing area of a third one of the support members is arranged at a distance from the illumination-observation plane which is greater than the distance of the first and/or second one of the support members, and wherein the bearing areas of the support members lie substantially in a base plane which is perpendicular to the illumination-observation plane,
wherein a projection of the center of gravity of the device in relation to the base plane lies in a direction perpendicular to the base plane between the bearing areas of the support members, and
wherein the projection of the center of gravity lies within a triangle defined by the three bearing areas of the three support members, whereby a stable stand of the hand-held color measurement device is achieved.

2. The hand-held color measurement device according to claim 1, wherein the first and the second support member are arranged on both sides of the measurement opening and substantially symmetrically with respect to it.

3. The hand-held color measurement device according to claim 1, wherein the bearing areas of the support members are each smaller than 20 mm$^2$, preferably smaller than 10 mm$^2$ and in particular smaller than 5 mm$^2$.

4. The hand-held color measurement device according to claim 1, wherein the distance between the base line and the illumination-observation plane measures at most 1 mm.

5. The hand-held color measurement device according to claim 1, wherein the distance between the base line and the illumination-observation plane measures at most 0.5 mm.

6. The hand-held color measurement device according to claim 1, wherein the distance between the base line and the illumination-observation plane measures 0 mm.

7. The hand-held color measurement device according to claim 1, wherein the pin-shaped support members are equipped with sensors, in particular pressure sensors, which cooperate with the controller in such a way as to monitor and signal whether all the support members are correctly placed on the surface of the measurement object.

* * * * *